(12) United States Patent
Schaible et al.

(10) Patent No.: US 9,763,739 B2
(45) Date of Patent: Sep. 19, 2017

(54) ROBOTIC HAND CONTROLLER

(71) Applicant: TITAN MEDICAL INC., Toronto (CA)

(72) Inventors: Uwe Schaible, Ancaster (CA); Drazena Brocilo, Ancaster (CA); John Harmen, Mississauga (CA)

(73) Assignee: TITAN MEDICAL INC., Toronto (CA)

(*) Notice: Subject to any disclaimer, the term of this patent is extended or adjusted under 35 U.S.C. 154(b) by 785 days.

(21) Appl. No.: 13/660,328

(22) Filed: Oct. 25, 2012

(65) Prior Publication Data
US 2013/0197538 A1 Aug. 1, 2013

Related U.S. Application Data

(62) Division of application No. 12/583,351, filed on Aug. 19, 2009, now Pat. No. 8,332,072.

(60) Provisional application No. 61/189,778, filed on Aug. 22, 2008.

(51) Int. Cl.
*B25J 17/00* (2006.01)
*A61B 19/00* (2006.01)
*B25J 9/16* (2006.01)
*A61B 34/30* (2016.01)

(52) U.S. Cl.
CPC .......... *A61B 19/2203* (2013.01); *A61B 34/30* (2016.02); *B25J 9/1633* (2013.01); *G05B 2219/35419* (2013.01); *G05B 2219/39439* (2013.01); *G05B 2219/40144* (2013.01); *G05B 2219/45117* (2013.01)

(58) Field of Classification Search
USPC ..... 74/490.01, 490.06, 501.6, 491; 901/4, 5, 901/9, 10; 414/5, 792.9, 909; 601/125; 606/1
See application file for complete search history.

(56) References Cited

U.S. PATENT DOCUMENTS

| | | | | |
|---|---|---|---|---|
| 4,216,467 A * | 8/1980 | Colston | ............................ | 341/20 |
| 5,116,180 A * | 5/1992 | Fung et al. | ........................ | 414/5 |
| 5,193,963 A | 3/1993 | McAffee et al. | | |
| 5,631,861 A * | 5/1997 | Kramer | ............................... | 703/7 |
| 6,377,011 B1 * | 4/2002 | Ben-Ur | ........................... | 318/566 |
| 7,138,976 B1 * | 11/2006 | Bouzit et al. | ................. | 345/156 |
| 7,390,157 B2 * | 6/2008 | Kramer | ............................... | 414/5 |
| 7,453,227 B2 | 11/2008 | Prisco et al. | | |
| 7,480,600 B2 * | 1/2009 | Massie et al. | ..................... | 703/6 |
| 7,505,030 B2 | 3/2009 | Cunningham et al. | | |
| 7,991,509 B2 | 8/2011 | Lipow | | |

(Continued)

FOREIGN PATENT DOCUMENTS

| | | |
|---|---|---|
| EP | 1690652 A1 | 8/2006 |
| EP | 1876504 A1 | 1/2008 |
| EP | 1876505 A1 | 1/2008 |

*Primary Examiner* — Zakaria Elahmadi
(74) *Attorney, Agent, or Firm* — Perry + Currier Inc.

(57) ABSTRACT

A hand controller for enabling a user to perform an activity and method for controlling a robotic arm is provided. The hand controller includes a bar with a grip and a plurality of motors to provide a force feedback to the user in response to the movement of the plurality of mechanical arms. The method involves receiving input corresponding to the manipulation of a bar and providing a force feedback in response to the movement of the plurality of mechanical arms.

10 Claims, 5 Drawing Sheets

(56) References Cited

U.S. PATENT DOCUMENTS

| | | |
|---|---|---|
| 8,142,420 B2* | 3/2012 | Schena .............................. 606/1 |
| 8,162,926 B2* | 4/2012 | Schena .............................. 606/1 |
| 8,167,872 B2* | 5/2012 | Schena .............................. 606/1 |
| 8,167,873 B2* | 5/2012 | Schena .............................. 606/1 |
| 8,277,443 B2* | 10/2012 | Jinno ................................ 606/1 |
| 8,368,641 B2 | 2/2013 | Tremblay et al. |
| 2002/0120254 A1 | 8/2002 | Julian et al. |
| 2003/0083648 A1 | 5/2003 | Wang et al. |
| 2004/0111183 A1 | 6/2004 | Sutherland et al. |
| 2004/0116906 A1* | 6/2004 | Lipow ................................ 606/1 |
| 2004/0243147 A1 | 12/2004 | Lipow |
| 2005/0102062 A1 | 5/2005 | Green |
| 2005/0183532 A1* | 8/2005 | Najafi et al. ................ 74/490.01 |
| 2006/0149418 A1 | 7/2006 | Anvari |
| 2007/0083098 A1 | 4/2007 | Stern et al. |
| 2010/0063630 A1 | 3/2010 | Sutherland et al. |
| 2010/0139437 A1* | 6/2010 | Ichikawa et al. .......... 74/490.05 |
| 2013/0175103 A1* | 7/2013 | Flowers ....................... 180/65.1 |

* cited by examiner

ROBOTIC HAND CONTROLLER

CROSS REFERENCE TO RELATED APPLICATION

This application is a divisional of U.S. patent application Ser. No. 12/583,351 filed on Aug. 19, 2009, which claims priority of U.S. Provisional Application No. 61/189,778 filed Aug. 22, 2008, all of which are incorporated by reference herein.

FIELD OF INVENTION

The invention disclosed here relates in general to a field of robotic instruments, and more particularly, to a hand controller for a robotic system for use in surgery.

BACKGROUND

With the gradual transition of medical surgery from the conventional process of making a long incision in the patient's body for performing a surgery to the next generation of surgery, i.e. minimal invasive surgery (MIS), continuous research is going on to develop and integrate robotic instruments in a system which can be used for MIS purposes. Such integration can help a surgeon to perform a surgery in an error-free manner, and at the same time to work in a realistic environment that gives the surgeon a feel of conventional surgery.

MIS is performed by making small incisions, in the range of 1-3 cm, in the patient's body and using pencil-sized instruments for the surgery. Most of the available robotic instruments used for MIS include one or more straight, elongated shafts, hereinafter referred to as robotic arms, which enter into the patient's body through the small incisions. The robotic arms can carry imaging equipment, such as a camera, as well as pencil-sized surgical instruments, such as forceps and scissors. The pencil-sized surgical instruments are also known as the end effectors. Further, the robotic arms are controlled from a robotic console which includes a robotic hand controller. The robotic hand controller receives input from the surgeon and in turn controls the motion of the robotic arm.

In the present state of the art, the robotic console does not include a haptic interface coupled with the robotic hand controller to provide force feedback to the surgeon. The human wrist is capable of three degrees of freedom, whereas the robotic arms provide more than four degrees of freedom at the site of surgery. The robotic hand controller could potentially command action and receive force feedback from the robotic arms. However, in the existing systems the force feedback is not received in any of the available degrees of freedom. Due to the absence of force feedback, the surgeon is forced to rely solely on the visual feedback received through the robotic console monitors. As a result, the surgeon does not get a real feel of conventional surgery.

Further, as the surgeon needs to perform various actions such as grasping and cutting of tissue during the surgery, the absence of force feedback makes it difficult to gauge the pressure being applied at the surgery site and hence, makes it difficult to conduct the surgery safely. Moreover, the time required for the surgery increases. Additionally, this poses a problem for novice and trainee surgeons as they might not be able to translate the visual feedback into optimum pressure, thereby leading to complications or serious injury. Furthermore, the time a surgeon spends in order to get trained on the MIS system increases significantly.

Adding to the above, the entire control of articulating and navigating the robotic arms, and hence the end effectors, rests in the hands of the surgeon operating on the robotic console. However, because of the excessive dependence on visual feedback and the virtual environment of MIS, a lot of inconvenience is caused to the surgeon leading to fatigue which hampers the efficiency of the surgeon.

SUMMARY

In light of the foregoing discussion, there is a need for a simple system and method of integrating a robotic hand controller having multiple degrees of freedom with force feedback mechanisms in a more efficient and improved manner. As the entire control of articulating and navigating the end effector rests in the hand of the surgeon, it is desirable that the robotic hand controller should provide a virtual environment as real as possible so as to reduce the requirement of visual judgment and hence, probability of errors. Further, the hand controller should preferably reduce fatigue and limit the inconvenience caused to the surgeon due to prolonged use.

BRIEF DESCRIPTION OF THE DRAWINGS

The preferred embodiments of the invention will hereinafter be described in conjunction with the appended drawings provided to illustrate and not to limit the invention, wherein like designations denote like elements, and in which.

DETAILED DESCRIPTION OF THE INVENTION

Figure 1:
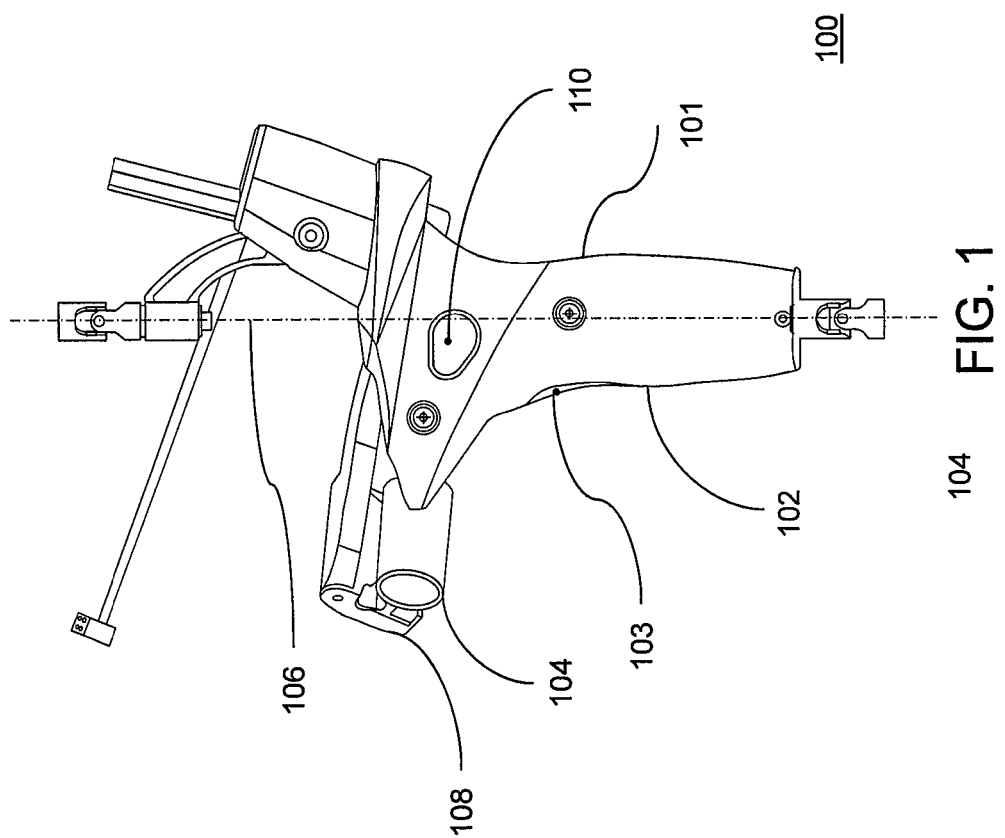
FIG. 1 illustrates a left side-view of a robotic hand controller, in accordance with an embodiment of the present invention.

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention.

In an embodiment, a robotic system for use in a medical activity, namely Minimal Invasive Surgery (MIS), is described. The system includes a console which can be a robotically manipulated console to be worked upon by a surgeon to perform an operation. For the purpose of this description the term "console" and "robotic console" have been used interchangeably hereinafter. The robotic console further includes a hand controller wherein the hand controller is a robotic hand controller along with a force feedback or haptic interface. The terms "hand controller" and "robotic hand controller" are henceforth used interchangeably. The hand controller has a bar with a grip which enables a user, in this case a surgeon, to hold and manipulate it. The haptic interface connects the robotic system and the surgeon through a sense of touch, also known as kinesthetic stimulation or force feedback. The force feedback is created and transferred to the surgeon using motors capable of generating counterforces and vibrations.

The robotic hand controller 100 of the present invention can control high precision medical tools/manipulators attached to a mechanical arm wherein the mechanical arm can be a robotic arm. The terms "mechanical arm" and "robotic arm" are henceforth used interchangeably. Such robotic systems can include a plurality of robotic arms and one or more medical tools. The medical tools are mounted on the robotic arms preferably at the distal end of the robotic arms. The medical tools can also be referred to as end effectors where the end effectors are used to work upon a work piece, in this case a patient, to perform an activity. The terms "medical tool" and "end effector" are henceforth used interchangeably. The mechanical arms assembly comprising a mechanical arm and a medical tool or end effectors can be used in medical robotic surgery, endoscope or other medical inspection devices, aerospace industry devices, simulator interfaces etc. The medical tools that can be attached to the robotic arms can be a forceps, scissors, a needle driver, an imaging device or any other type of medical tool or end effectors already known to a person of ordinary skill in the art. The robotic arms, already known in the art, are fitted with a plurality of sensors such as force transducers which can measure forces acting on the arm while performing a surgical procedure. Further, the end effectors are also fitted with a plurality of force transducers which can sense forces acting on them while performing a surgical procedure. The measured forces are converted into signals which are sent to the robotic hand controller 100 where they are interpreted by a force feedback device i.e. the haptic feedback interface. A processor, namely a processing and control module present in the robotic hand controller 100, interprets the signal. Force feedback is produced by a plurality of motors based on the received signals. Typically, force feedback is created by utilizing a DC motor either directly or indirectly coupled to a position encoder. The encoder output signals are used to determine the rotational position of the DC motor shaft, and the electrical supply to the DC motor is modulated so as to produce a motor torque that opposes the direction of motion sensed by the encoder. The force feedback produced is a replica of the forces acting at the site of the surgery. The robotic arms are capable of operating in a plurality of degrees of freedom. Thus, the robotic hand controller 100 of the present invention in combination with the robotic arms is able to receive force feedback in all the available 8 degrees of freedom. The robotic hand controller 100 has been designed for multiple operator command environments and for multiple types of users with differing hand sizes, palm sizes, finger size, grip strengths etc. In such usage, the robotic hand controller environments can range from the hospital operating room to aerospace or to other environments where a high fidelity robotic hand controller is required to command a robotic arm. In the instance of robotic surgery, the hand controller is connected and positioned directly under the robotic viewing console in an ergonomic position for the surgeon. Therefore, the surgeon can view the surgical site on the console screen and manipulate the hand controllers simultaneously.

Figure 2:
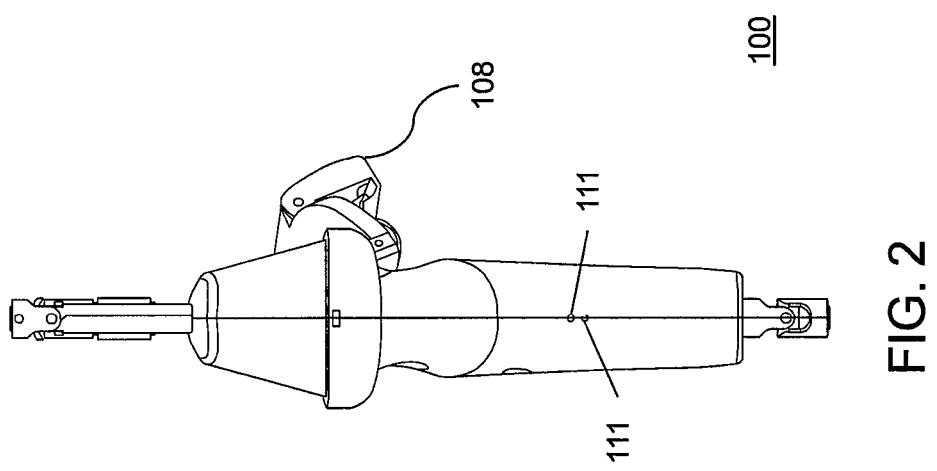
FIG. 2 illustrates a back-view of a robotic hand controller, in accordance with an embodiment of the present invention.
Figure 3:
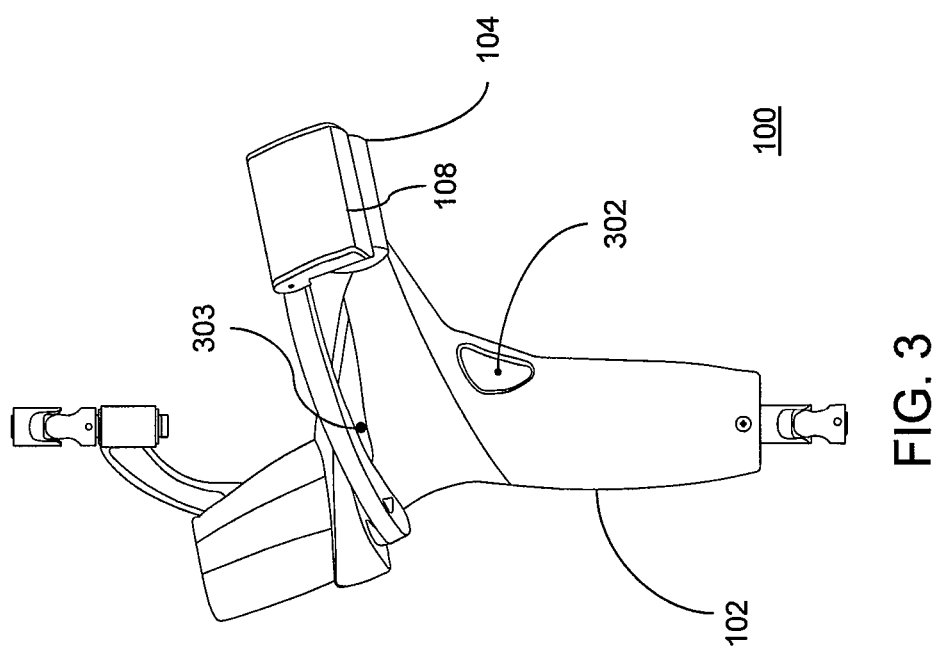
FIG. 3 illustrates a right side-view of a robotic hand controller, in accordance with an embodiment of the present invention.

FIG. 1 illustrates a left side-view of a robotic hand controller 100, in accordance with an embodiment of the present invention. FIG. 2 illustrates a back-view of the robotic hand controller, in accordance with an embodiment of the present invention. Further, FIG. 3 illustrates a right side-view of the robotic hand controller, in accordance with an embodiment of the present invention. The robotic hand controller 100 internally features electronic circuitry, sensors and motors in order to operate and receive force feedback from the plurality of end effectors of the plurality of robotic arms (not shown). These features are described in more detail with reference to FIG. 4.

The electronic circuitry, sensors and motors used in the present invention may be sourced from a variety of different manufacturers and are readily available in different types and configurations already known to a person of ordinary skill in the art. Further, the electronic circuitry and sensors are housed in an exoskeleton which is ergonomically designed to support the hands of a surgeon. Moreover, the robotic hand controller 100 can receive, as well as send, signals as per the motion of the plurality of robotic arms and the end effectors within a haptic environment.

Additionally, the robotic hand controller 100 provides the full natural motion of the wrists, hands, and fingers in order to have the feel of conventional surgery. Moreover, the robotic hand controller 100 also provides additional degrees of freedom. The available degrees of freedom with the robotic hand controller 100 are: motion in the translational planes i.e. the X, Y and Z planes of a co-ordinate system readily known to a person of ordinary skill in the art; movement of the end effectors, i.e. pitch, yaw, roll; a natural open/close action of a surgeon's fingers leading to the interface of the index finger with the thumb (pinching action); and an activation mode (vibrate). The robotic hand controller 100 has a bar 101 with a grip 102 for the user to place his hand to operate and control the robotic hand controller 100. For exhibiting the pinching motion, the robotic hand controller 100 allows a natural placement of the hand on the grip 102 and of the index finger in the slot 104 of the robotic controller 100, as shown in FIG. 1. The axis of motion for the fingers is displaced to the right of the central axis 106 (i.e., behind the plane of FIG. 1) due to the placement of elements 104 and 108 for yaw motion of the robotic hand controller 100. This placement provides a natural interface between the thumb resting on the bar and the index finger present in the slot 104 to provide effortless pinching motion.

In an embodiment, the robotic hand controller 100 can allow for a flexible adjustment of the index finger ring 104 based on the index finger cross section and length of the user hand. In an embodiment, a multiple number of interchangeable index finger rings (not shown in the figures) can be used for this purpose. The index finger rings can be slotted into the robotic hand controller 100 structure. Additionally, a slider structure 108, with multiple notches can allow finger length adjustment to the surgeon.

The robotic hand controller 100 can provide force feedback to the surgeon in all the available eight degrees of freedom (8DOF), as described above, when operated in conjunction with a commercial off the shelf (COTS) device. The COTS device is either a robotic arm or a total MIS set-up where the improved robotic hand controller 100 of the present invention replaces the existing hand controller. The available force feedback in all the 8DOF from the robotic hand controller 100 improves the control of the robotic arms in all the available degrees of freedom. Also, the force feedback can be received at the slot 104, taking the virtual surgery environment closer to an open conventional surgery. Further, by altering the type, rating, housing, or location of the index finger force transducer (not shown) provided for feedback control, the finger command fidelity can be modified as required in slot 104. The force transducer used in the present invention is an elastomer-based composite material type sensor manufactured and supplied by CUI Inc. and described under U.S. Pat. No. 6,558,577 B1. Other types of force transducers may be utilized including piezo-resistive elements, resistive strain gauges, load cells, and other types already known to a person of ordinary skill in the art.

The vibration motion or force feedback assists the surgeon to effectively interpolate the pressure being applied by him at the surgery site while performing various actions such as grasping and cutting of tissue. The availability of force feedback in the form of vibrational motion to the surgeon can be varied by changing the type, rating, housing, or focus location of the motor being used for producing vibrations. This adjustment will help to match the surgeon's preference or particular environment of usage. As different surgeons might have different sensory perception levels, the vibrational motion generator or the vibration motor, hereinafter used interchangeably, used in the robotic hand controller 100 can be adjusted to produce the optimum amount of vibration motion or force feedback. The vibrational motion generator or the vibration motor used in the present invention is a flat type vibration motor sourced through SolarRobotics (www.solarbotics.com). The details of the vibrational motion generator or the vibration motor are described below. Other types of vibrational motion generators may be utilized, include piezo-electronic buzzers and/or electro-acoustic flexure discs, and any other types already known to a person of ordinary skill in the art. Further, the haptic force feedback can be improved by providing precise and specialized textural effects at the robotic hand controller 100 in the form of a tactile force feedback. The tactile force feedback is produced by using a computer software program.

In an embodiment, the robotic hand controller 100 can contain hand presence sensors 111 as shown in FIG. 2 or in general a position sensing device, to detect the presence of the hands on the exoskeleton of the robotic hand controller 100. The hand presence sensors 111 can further provide an active or hands-on mode and a shutdown or hands-off mode of the robotic hand controller 100. This can enable the movement of the plurality of the robotic arms when the surgeon takes control of the robotic hand controller 100 with his hands on the grip 102 of the robotic hand controller 100. Further, this can ensure that a mere touch or an accidental push, without the hands on the grip 102, will not translate into movement of the plurality of robotic arms. This can avoid occurrence of accidental damage to a patient due to unwanted or accidental movement of the plurality of robotic arms. The hand presence sensor used in the present invention is a reflective type Photomicrosensor, part no. EE-SY410 manufactured by Omron. Other types of hand presence and positional sensors or position sensing devices include capacitive touch sensors, thermal sensors, strain gauges, load cells, e-field sensors, piezo-resistive sensing elements, pressure pads and any other types already known to a person of ordinary skill in the art.

In various embodiments, the robotic hand controller 100 can include an actuator button 303, as shown in FIG. 3, to perform various actions, such as pinching, grasping and cutting. In another embodiment, the robotic hand controller 100 can further include a clutch mechanism in the form of a clutch button 103 as shown in FIG. 1, to allow the surgeon to re-center the robotic hand controller 100 into an ergonomic position without moving the plurality of robotic arms. The clutching mechanism can be performed by using an infrared beam break, optical presence and e-field sensing techniques or any other type of technique already known to a person of ordinary skill in the art. This will avoid inconvenience as well as fatigue to the surgeon. In yet another embodiment, the robotic hand controller 100 can have an end effector change button 302 as shown in FIG. 3. In a conventional surgical process the surgeon uses a variety of surgical devices to perform various operations like cutting, grasping, and pinching. To perform similar operations in an MIS set up, a plurality of robotic arms is provided with different end effectors attached to them. The end effector change button 302 upon actuation helps to switch among the plurality of robotic arms and to engage the required robotic arm for performing the desired operation. In various embodiments, the clutch button 103 or end effector change button 302 can have different sizes, positions, etc. based on the physical characteristics and convenience of the surgeon.

Furthermore, in an embodiment, the design of the robotic hand controller 100 can allow for an ambidextrous operation as the hand grip 102 is designed to be held with ease by both left and right handed surgeons. In another embodiment, the robotic hand controller 100 can have an ergonomic design to allow comfortable operation by one or more surgeons having different hand characteristics, such as palm size, finger size, grip strengths etc. This ergonomic design of the structure of the robotic hand controller 100 helps to prevent operator or user fatigue and increase usage convenience.

Further, the robotic hand controller 100 can be connected to any commercial off the shelf (COTS) device in order to provide it with the translational planes (x, y, z) of force feedback. Since a system is made up of numerous components and continuous R&D leads to newer and upgraded system components, using COTS components does away with the need of an over-all system development. Thus, whenever an improved version of a component is readily available in the market, the component can be directly embedded into the overall system. Similarly, in the present invention, the robotic hand controller 100 can be integrated with the readily available robotic consoles for MIS. Moreover, this serves a dual purpose as it saves time for developing a fitting robotic hand controller for the developed robotic consoles or vice-versa.

Figure 4:
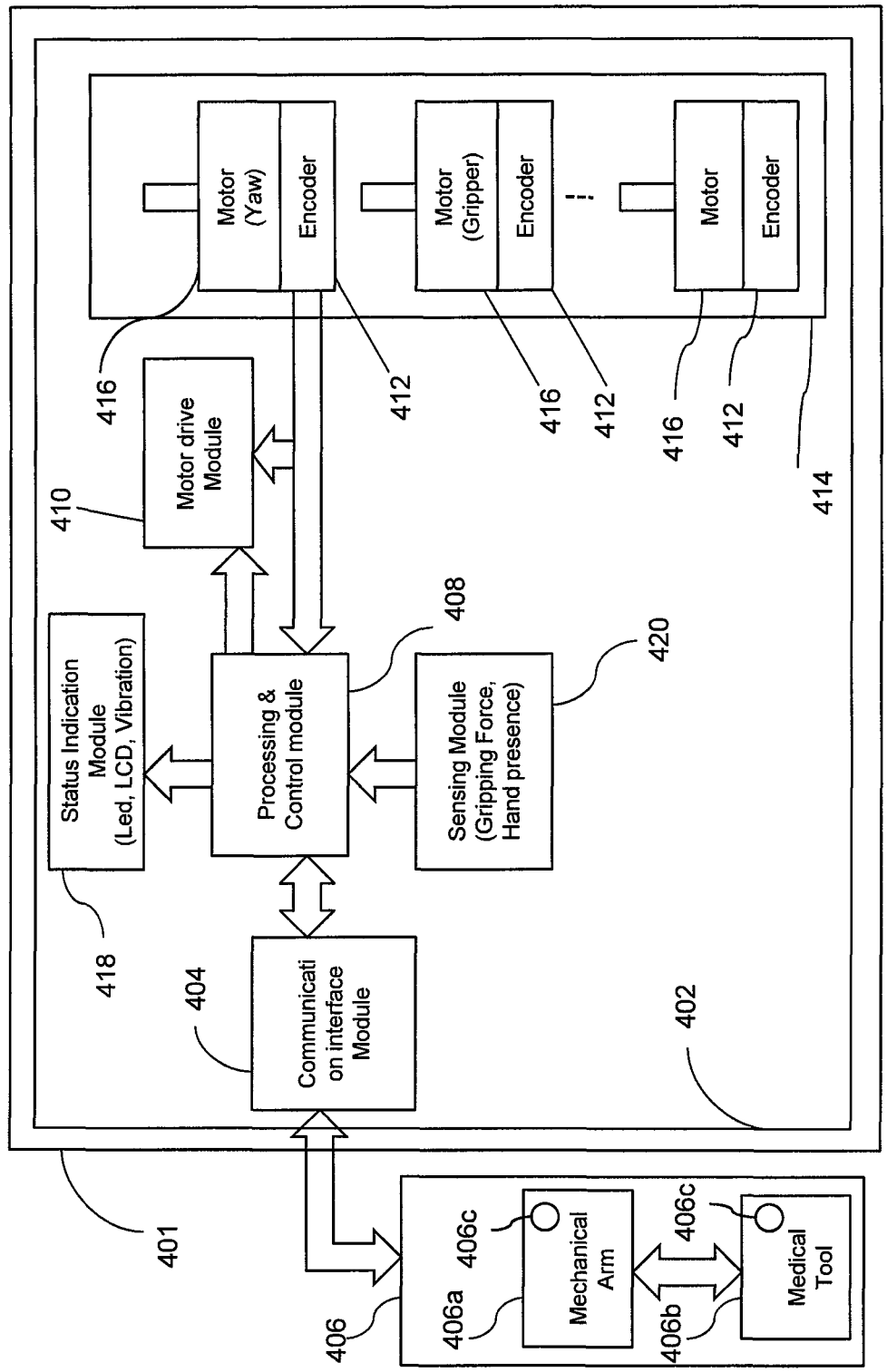
FIG. 4 illustrates a block diagram of the electronic circuitry of the robotic hand controller, in accordance with an embodiment of the present invention.

FIG. 4 shows a block diagram 400 of the electronic circuitry of the robotic hand controller 100 connected with the mechanical arm assembly in accordance with an embodiment. The block diagram 401 of the robotic hand controller 100 houses the electronic circuitry of the force feedback device as shown in the block 402. A communication module, namely a Communications Interface Module 404, includes associated electronic circuitry that is used to send and receive force, status and control commands to and from the mechanical arm assembly 406. The mechanical arm assembly further comprises a mechanical arm 406a and a medical tool 406b. Further, the mechanical arm 406a and the medical tool 406b each include a sensor 406c where the sensor can be a force sensor or a force transducer as mentioned above. The force sensor 406c senses the force acting on the mechanical arm 406a and the medical tool 406b and sends the signal corresponding to the force sensed to the Communication Interface Module 404. In one embodiment, the Communications Interface Module 404 may be hardwired to the mechanical arm assembly 406 and transfer command messages using CANbus, USB, RS-232/485, Firewire, DSL, Ethernet or other standard and non-standard physical layers well known to those skilled in the art. In yet another embodiment, the Communications Interface Module 404 may be connected wirelessly to the mechanical arm assembly 406 using either an optical or RF based transceiver. Such a wireless transceiver may use standard SONET, SDH, Zigbee, Wi-Fi, Bluetooth or other standard and non-standard physical layers well known to those skilled in the art. The Communications Interface Module 404 interprets the force, status and control commands and transfers information to and from the Processing and Control Module 408. A microprocessor in the Processing and Control Module 408 receives the force, status and control command information from the Communications Interface Module 404 and generates the appropriate command signals for the Motor Drive Module 410. The Motor Drive Module 410 measures the positional information generated by the Motor Encoders 412 signals, and controls the electrical excitation to the plurality of vibration motors 416 shown in the block 414 of the block 401, thereby generating a desired level of haptics feedback force along the various axes of hand and digit motion. The haptics feedback is generated by the plurality of vibration motors 416 shown in the block 414 where the motors 416 are the vibrational motion generators or the vibration motors mentioned above. These motors are also referred to as "actuators". The Motor Encoders 412 signals are also read by the Processing and Control Module 408 where they are used to generate control commands that are sent to the mechanical arm assembly 406 via the Communications Interface Module 404. The Status Indication Module 418 receives status information from the Processing and Control Module 408 and activates a plurality of status indication means, including but not limited to LEDs, audible buzzer and/or an LCD display. The Status Indication Module 418 also controls the output of auxiliary haptics feedback devices integrated into the block 401, including but not limited to vibration motors, piezo-electronic buzzers and/or electro-acoustic flexure discs. Additional haptics feedback information is measured in the block 401 through the Sensing Module 420. Electrical signals from a plurality of force and positional presence sensors may be interfaced to the Sensing Module 420 to generate force and status information that is sent to and interpreted by the Processing and Control Module 408. This force and status information is in turn transferred by the Processing and Control Module 408 to the mechanical arm assembly 406 via the Communications Interface Module 404.

One embodiment of the present invention houses all of the modules which are part of the electronic circuitry of the robotic hand controller 100 illustrated in FIG. 4 within the block 401. Another embodiment of the present invention would house the Communications Interface Module 404 externally to the block 401. Yet another embodiment of the present invention would house both the Communications Interface Module 404 and the Processing and Control Module 408 externally to the block 401. Still another embodiment of the present invention would house the Communications Interface Module 404, the Processing and Control Module 408, and the Motor Drive Module 410 externally to the block 401. All the modules mentioned in the block diagram 400 are part of the electronic circuitry of the robotic hand controller 100 except for the mechanical arm assembly 406. These modules are electronic circuits which preferably have software programs embedded into them.

Further, in an embodiment of the present invention the signal from the index finger force transducer is received at the Sensing Module 420 of the block 401 to calculate the additional haptics information. In another embodiment of the present invention the signal from the index finger force transducer is received at the Status Indication Module 418 of the block 401 to calculate the additional haptics information. In yet another embodiment of the present invention the signal from the index finger force transducer is received at the Processing and Control Module 408 of the block 401 to calculate the additional haptics information. In yet another embodiment of the present invention the signal from the index finger force transducer is received at the Sensing Module 420 or the Status Indication Module 418 or the Processing and Control Module 408 present externally to the block 401 to calculate the additional haptics information.

Figure 5:
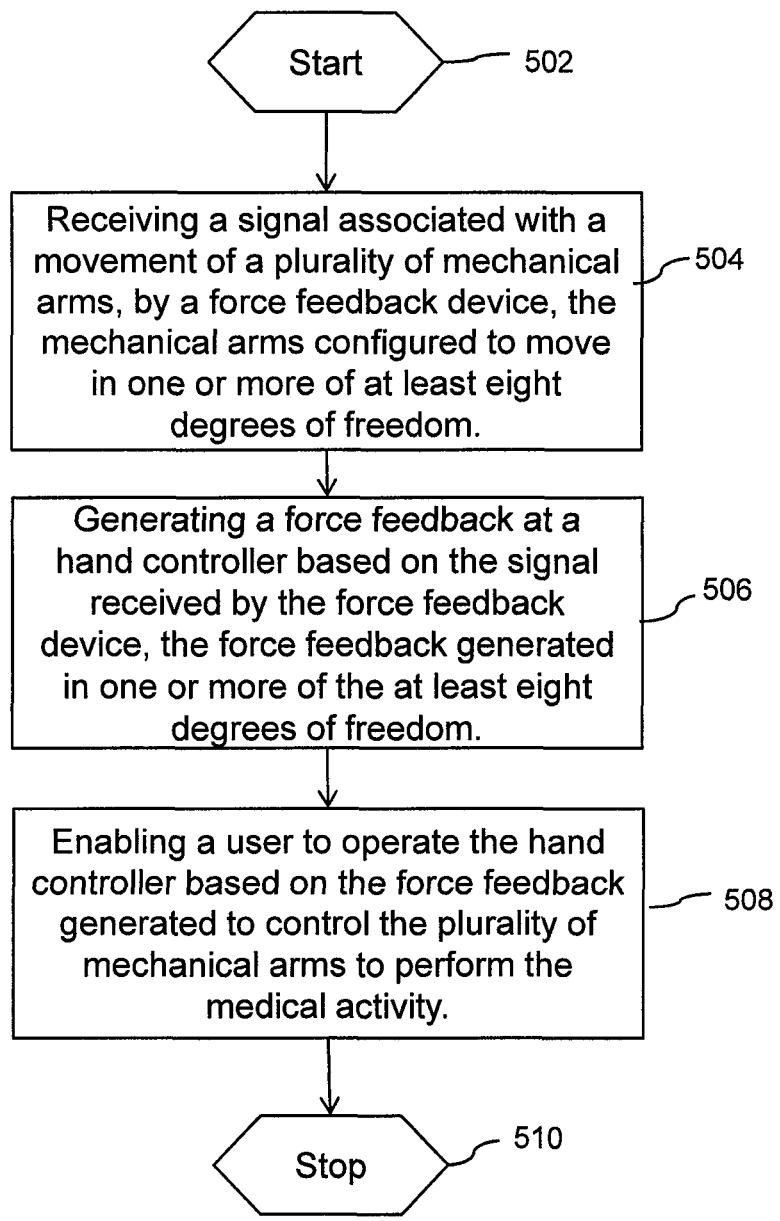
FIG. 5 is a flow diagram illustrating a method for receiving a force feedback at the hand controller to perform a medical activity, in accordance with an embodiment of the present invention.

FIG. 5 is a flow diagram 500 illustrating a method for receiving a force feedback at the hand controller 100 to perform a medical activity, the components of which have been described in FIG. 1, FIG. 2, FIG. 3 and FIG. 4. The method starts at 502. At 504, the method is described wherein the force feedback device receives a signal based on the force sensed by a plurality of mechanical arms, the plurality of mechanical arms configured to move in one or more of at least eight degrees of freedom, as described in FIG. 1. Thereafter at 506, force feedback is generated at the hand controller 100 based on the signal received by the force feedback device from the force sensed by the mechanical arms, the force feedback being generated in one or more of the at least eight degrees of freedom. At 508, the force feedback generated at the hand controller enables a user, generally a surgeon, to operate the hand controller to perform a medical activity as described in FIG. 1. The method ends at 510.

Various embodiments of the present invention offer one or more advantages. The present invention provides a system and method for integrating the robotic hand controller 100, preferably having 8DOF, with force feedback mechanisms in all available degrees of freedom. Further, the combination of haptic and visual feedback in all the degrees of freedom provides the surgeon with a multi-sensory interface which helps in improving the accuracy and consistency of the surgical procedure.

What is claimed is:

1. A hand controller configured to enable a user to perform an activity, the hand controller comprising:
  a bar with a grip, the bar configured to be held and operated by the user to control a plurality of mechanical arms;
  a clutch button configured to allow a movement of the hand controller without a corresponding movement of any one of the plurality of mechanical arms for re-centering the hand controller; and
  a plurality of motors, the plurality of motors configured to provide a force feedback to the user in response to the movement of the plurality of mechanical arms in one or more of at least eight degrees of freedom.

2. The hand controller according to claim 1, wherein the bar is configured to control the plurality of mechanical arms in one or more of at least eight degrees of freedom.

3. The hand controller according to claim 1, wherein the bar is configured to be operated ambidextrously.

4. The hand controller according to claim 1, wherein the bar is configured to be held by multiple users, each user having a different hand size.

5. The hand controller according to claim 1, further comprising a position sensing device configured to sense presence of a hand of the user.

6. The hand controller according to claim 1, further comprising an index finger slot configured to receive an index finger of the user.

7. The hand controller according to claim 6, wherein the index finger slot comprises a force sensing device configured to sense a force being applied at the index finger slot by the index finger for operating a medical tool.

8. The hand controller according to claim 6, further comprising an element for supporting the index finger slot, the element connected to the bar.

9. The hand controller according to claim 8, wherein the element is pivotally connected to the bar at a pivot point.

10. The hand controller according to claim 9, wherein the pivot point is positioned off a central axis to provide a natural pinching motion.

* * * * *